(12) United States Patent
Godec

(10) Patent No.: US 7,662,637 B2
(45) Date of Patent: Feb. 16, 2010

(54) SENSITIVE DETECTION OF UREA AND RELATED COMPOUNDS IN WATER

(75) Inventor: Richard D. Godec, Longmont, CO (US)

(73) Assignee: GE Analytical Instruments, Boulder, CO (US)

(*) Notice: Subject to any disclaimer, the term of this patent is extended or adjusted under 35 U.S.C. 154(b) by 721 days.

(21) Appl. No.: 10/498,180

(22) PCT Filed: Dec. 2, 2002

(86) PCT No.: PCT/US02/38250

§ 371 (c)(1),
(2), (4) Date: Jan. 10, 2005

(87) PCT Pub. No.: WO03/048382

PCT Pub. Date: Jun. 12, 2003

(65) Prior Publication Data

US 2005/0106650 A1   May 19, 2005

(51) Int. Cl.
*G01N 33/00* (2006.01)
*C12M 1/34* (2006.01)
*C12M 3/00* (2006.01)

(52) U.S. Cl. ............... 436/146; 435/12; 435/287.1; 435/287.5; 435/288.3; 435/288.6; 436/108; 436/52; 436/145; 436/147

(58) Field of Classification Search ........... 435/12, 435/287.1, 288.6, 287.5, 288.3; 436/108, 436/146, 52, 145, 147

See application file for complete search history.

(56) References Cited

U.S. PATENT DOCUMENTS

| 3,915,804 | A | 10/1975 | Messing |
| 3,926,734 | A | 12/1975 | Gray et al. |
| 4,153,513 | A | 5/1979 | Edelmann et al. |
| 4,209,299 | A | 6/1980 | Carlson |
| 5,132,094 | A | 7/1992 | Godec et al. |
| 5,141,717 | A * | 8/1992 | McRae ............... 422/82.01 |
| 5,556,760 | A | 9/1996 | Nakamura et al. |
| 6,521,184 | B1 * | 2/2003 | Edgson et al. ........ 422/82.02 |
| 6,733,984 | B2 * | 5/2004 | Delwiche et al. ......... 435/12 |

OTHER PUBLICATIONS

Botre et al, "Carbonic anhydrase and urease: an investigation in vitro on the possibility of a synergic action," Biochimica et biophysica acta, 997, 111-114, 1989.*

* cited by examiner

*Primary Examiner*—William H Beisner
*Assistant Examiner*—Nathan A Bowers
(74) *Attorney, Agent, or Firm*—David Silverstein; Andover-IP-Law

(57) ABSTRACT

Methods and apparatus (FIG. 4a) are disclosed for selective and very sensitive detection of certain hydrolyzable compounds, especially urea, in water by hydrolyzing said hydrolyzable compounds in a sample of the water to one or more carbon dioxide group compounds and determining the difference in the carbon dioxide content of the water and the hydrolyzed sample using conductivity measurements or other carbon dioxide detector outputs.

32 Claims, 11 Drawing Sheets

SENSITIVE DETECTION OF UREA AND RELATED COMPOUNDS IN WATER

FIELD OF THE INVENTION

The invention relates generally to methods and apparatus for selective and sensitive detection of certain hydrolyzable organic compounds, particularly urea, in water. The invention is particularly useful in detecting such compounds in water at levels ranging from about 100 ppb as carbon to at least as low as 0.10 to 0.15 ppb. Such sensitive detection of such low levels of such compounds in water is especially useful for monitoring ultrapure water ("UPW") used in highly sensitive industrial applications such as in semiconductor manufacture, in fabrication of "acid-activated, chemically-amplified photoresists" and in other applications which are highly sensitive to low levels of chemical contamination.

More particularly, sensitive detection of urea in water samples in accordance with the invention comprises inline hydrolysis of urea to one or more of the compounds carbon dioxide, carbonic acid, bicarbonate and/or carbonate (hereinafter "the carbon dioxide group") and ammonia ($NH_3$) and/or ammonium ion ($NH_4^+$), preferably with urease, most preferably with immobilized urease, in combination with the sensitive measurements of the concentrations of such carbon dioxide group in samples prior to and after such hydrolysis. A preferred sensitive measurement uses $CO_2$-selective membrane technology to transfer at least some $CO_2$ per se from a water sample in a first compartment across a membrane into a second compartment containing deionized ("DI") water. The difference in conductivities prior to and after hydrolysis of a sample or samples can be used as a means to detect urea contamination. Other $CO_2$ specific detection methods and apparatus well known in the art, such as Non-Dispersive Infra-Red ("NDIR") photometry, may also be used for this purpose.

This technology can be readily adapted to detect very low levels of other organic nitrogen compounds in water. The technology of this invention can be utilized, for example, to prevent contamination of photolithography tools and environment used in fabricating acid-activated, chemically-amplified photoresists by organic nitrogen compounds and their decomposition products. Other applications of this technology will be readily apparent to those skilled in this art, and all such applications are considered to be within the scope of this invention.

BACKGROUND OF THE INVENTION

The invention is based in part on membrane technology such as that taught by U.S. Pat. Nos. 4,209,299 (Carlson '299) and 5,132,094 (Godec et al. '094), which are incorporated herein by reference. It is not practical, however, sensitively to detect and measure urea or related compounds in ultrapure water by means of urease conversion to $CO_2$ and $NH_3$ using the membrane-based method of Carlson '299 because any presence of trimethylamine, another common contaminate of ultrapure water, would interfere. U.S. Pat. No. 3,915,804 (Messing '804), which is also incorporated herein by reference, teaches that decomposition of urea in water with urease will produce a change in conductivity of the water. This method, however, is complicated by ionic contamination by other ionic extractables from urease, urease substrate or support, and/or the apparatus. Any presence of these ionic contaminations will compromise correct determination of urea concentration, especially when the urea concentration is very low or where very accurate determinations of urea concentration are required.

U.S. Pat. No. 3,926,734 (Gray et al. '734), which is also incorporated herein by reference, uses a bed of immobilized urease to hydrolyze urea to ammonium ion. Following adjustment of the pH to 11 to form ammonia, the latter is selectively passed through a membrane and pH is measured. This method, however, will also measure volatile amine compounds, such as trimethylamine, that are found in ultrapure water, and therefore produces an incorrect measure of urea.

U.S. Pat. Nos. 4,153,513 (Edelmann et al. '513) and 4,277,560 (Gray et al. '560), which are also incorporated herein by reference, teach methods and apparatus that involve injection of an unknown sample into a flowing buffer stream or other solution. This method will dilute urea concentration in the sample to a much lower concentration thereby making very low level measurements even more difficult or impossible (e.g., if the concentration is lowered below the instrument detection limit).

U.S. Pat. No. 4,476,005 (Tokinaga et al. '005), which is also incorporated herein by reference, describes an electrode consisting of a special urease-immobilized membrane and a selective ammonium ion electrode. The membrane has added amino groups to increase the permeation rate of ammonium ion. This electrode is an improvement over one described by G. G. Guilbault in *Handbook of Enzymatic Method of Analysis*, (Marcel Dekker, New York 1976) and is faster and more sensitive. However, both of these methods and apparatus are not sensitive enough for measurement of urea in trace concentrations in ultrapure water: Additionally, both of these electrodes will respond to other common contaminates such as trimethylamine.

U.S. Pat. No. 5,133,937 (Frackleton et al. '937), which is also incorporated herein by reference, teaches design of an apparatus that has a thermally controlled chamber for urease or other enzyme. The Frackleton et al. '937 patent, however, does not teach measurement of $CO_2$ to determine concentration of urea.

U.S. Pat. No. 5,556,760 (Nakamura et al. '760), which is also incorporated herein by reference, teaches a method and apparatus for measurement of urease enzyme on a surface of a solid. Urea is added to a chamber that is formed with one wall being the solid surface, and pH is measured to determine an amount of urease. This invention, however, does not measure $CO_2$ produced by urease hydrolysis of urea to $CO_2$ and $NH_3$.

Accordingly, there is no known prior art which teaches or suggests an online sensitive analyzer and methods for detecting urea (or other related compounds which produce members of the carbon dioxide group upon hydrolysis) in ultrapure water or use of such an apparatus to prevent contamination of acid-catalyzed photoresists and of a fabrication facility (fab) for preparing such photoresists. Apparatus and methods or entities invention overcome in whole or in part limitations and deficiencies of the prior art.

OBJECTS OF THE INVENTION

Accordingly, a general object of this invention is to provide apparatus and methods for low-level detection and measurement in aqueous solutions of compounds or entities hydrolyzable to one or more members of the carbon dioxide group as herein defined.

It is a principal object of this invention to provide apparatus and methods for detection of compounds or entities, specifically urea, hydrolyzable to one or more members of the carbon dioxide group, such compounds being present in ultrapure water used in fabricating acid-activated, chemically-amplified photoresists and in similar applications which are sensitive to even very low-levels of chemical contamination.

A specific object of this invention is to provide apparatus and methods to prevent contamination by compounds, particularly urea, hydrolyzable to members of the carbon dioxide group or decomposition products of such compounds, of acid-activated, chemically-amplified photoresists, of lithography tools used to fabricate semiconductors, and of Facilities in which they are fabricated.

Other objects and advantages of this invention will in part be obvious and will in part appear hereinafter. The invention accordingly comprises, but is not limited to, methods and related apparatus, involving the several steps and the various components, and the relation and order of one or more such steps and components with respect to each of the others, as exemplified by the following description and accompanying drawings. Various modifications of and variations on the methods and apparatus as herein described will be apparent to those skilled in the art, and all such modifications and variations are considered within the scope of the invention.

SUMMARY OF THE INVENTION

The present invention comprises an apparatus and methods for selective and sensitive detection of urea and related compounds in water. A preferred method consists of inline hydrolysis of urea to members of the carbon dioxide group and $NH_3$ and/or $NH_4^+$ using urease, preferably immobilized urease, in combination with sensitive measurement of concentrations of members of the carbon dioxide group, preferably $CO_2$ itself, before and after such hydrolysis. The methods and apparatus which sensitively measure members of the carbon dioxide group in a sample of water preferably use a $CO_2$-selective membrane to transfer at least some $CO_2$ from the water sample into a second chamber or region containing deionized water. The water sample may or may not be acidified and/or buffered to a predetermined pH substantially less numerically than the pK of the conventional or practical first ionization constant of carbonic acid. The conductivities of such deionized water and of $CO_2$-containing solution collected in or from said second chamber are measured, and a conductivity differential between these conductivities is established. Such conductivity differential is mathematically related to and can be correlated with $CO_2$ concentration in the original sample which, in turn, is mathematically related to and can be correlated with urea concentration in the original water sample.

By "conventional" or "practical" first ionization constant of carbonic acid is meant herein the quantity

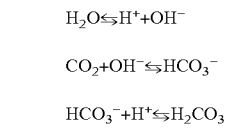

where ( ) indicates concentrations or activities expressed in gram formula weights (gram moles) per liter. The resulting K is that usually reported in handbooks as the "first ionization constant of $H_2CO_3$" it being a long tradition, as a practical or conventional matter, to regard the sum $(CO_2)+(H_2CO_3)$ as "$H_2CO_3$". It is well known however that as art actual matter $(CO_2)$, that is dissolved, unhydrated $CO_2$, is always about 50 times that of actual $(H_2CO_3)$, that is hydrated $CO_2$. The actual first ionization constant of $H_2CO_3$ per se is therefore about 50 times greater than the practical or conventional first ionization constant generally given in handbooks. Herein "first ionization constant" means such practical or conventional constant.

The rate of hydration of $CO_2$ is slow and apparently proceeds by the reactions:

$$H_2O \leftrightarrows H^+ + OH^-$$

$$CO_2 + OH^- \leftrightarrows HCO_3^-$$

$$HCO_3^- + H^+ \leftrightarrows H_2CO_3$$

Therefore, in a process such as the preferred method of the invention in which $CO_2$ is dissolved in water and the resulting electrical conductance measured, reaction time must be provided to allow substantial hydration of $CO_2$ per se.

In particular, this invention can be used to measure very small concentrations of urea in ultrapure water used to manufacture semiconductor circuits. It is important to prevent contamination of the new acid-catalyzed, chemically-amplified deep UV photoresists used in advanced photolithography to make the smallest images for highest density semiconductor circuits. This contamination can be a problem even at very low, e.g., sub part-per-billion (ppb) concentrations of basic gases such as ammonia. Hydrolyzable nitrogen compounds and other hydrolyzable compounds in purified water used for semiconductor manufacturing can transfer from the water and cause problems with the acid-catalyzed photoresist.

To prevent this from happening, it is critical accurately to measure urea and related compounds in semiconductor water substantially continuously. This requires the preferred, very sensitive detection methods and apparatus of this invention to measure urea. No other online continuous urea measurement method and apparatus is known to be as sensitive. This online urea analyzer may be used to measure urea substantially continuously, and may be used in conjunction with a process to remove or prevent urea or related organic nitrogen compounds present in ultrapure water from being sent to a fab for use in semiconductor processing where other portions of the system will be contaminated. There is no known prior art where an online analyzer so sensitive to urea in water is used to prevent the contamination of acid-catalyzed photoresists.

Additionally it is useful to measure levels of urea and/or related compounds at the beginning of a water purification process. This can also be done with the analyzer of this invention if the background level of carbon dioxide group compounds is not large relative to the level of such compounds produced by urease conversion of urea to ammonia and carbon dioxide group compounds. If such background level is too high, then background carbon dioxide group compounds can be removed by conventional techniques prior to conversion of urea by urease in accordance with this invention.

More particularly, apparatus for estimating as carbon dioxide the total of carbon dioxide, carbonic acid, bicarbonate and carbonate released by hydrolysis of hydrolyzable entities dissolved and/or dispersed in water containing such entities, in accordance with this invention comprises:

(a) a measuring system for obtaining from a first sample of said water a measure of total concentration of carbon dioxide, carbonic acid, bicarbonate and carbonate in said sample before hydrolysis;

(b) a hydrolysis system effective substantially to hydrolyze said hydrolyzable entities dissolved and/or dispersed in a second sample of said water whereby a hydrolyzed sample is obtained comprising carbon dioxide, carbonic acid, bicarbonate and/or carbonate and other hydrolysis products;

(c) a measuring system for obtaining from said hydrolyzed sample a measure of total concentration of carbon dioxide, carbonic acid, bicarbonate and carbonate in said hydrolyzed sample; and, (d) an estimating system for estimating from said measure of total concentration of carbon dioxide, carbonic acid, bicarbonate and carbonate in said first sample and from said total concentration of carbon dioxide, carbonic acid, bicarbonate and carbonate in said hydrolyzed sample, a measure as carbon dioxide of total carbon dioxide, carbonic acid, bicarbonate and carbonate released by hydrolysis of said hydrolyzable entities dissolved and/or dispersed in said water.

A hydrolysis system in accordance with this invention comprises one or more agents effective to hydrolyze entities which are hydrolyzed by urease, preferably urease, more preferably immobilized urease. A hydrolysis system of this invention also preferably comprises a membrane having juxtaposed to one surface thereof one or more hydrolytic agents effective to hydrolyze entities which are hydrolyzed by urease and having juxtaposed along another surface of said membrane a flow path for the second sample, the membrane being substantially impermeable to the one or more hydrolytic agents while being substantially permeable to urea and hydrolysis products thereof.

A hydrolysis system in accordance with this invention may also comprise a membrane substantially impermeable to one or more agents effective to hydrolyze entities which are hydrolyzed by urease while being substantially permeable to water, carbon dioxide, carbonic acid, bicarbonate and carbonate. A hydrolysis system in accordance with this invention may further comprise a mixing and contacting element to commingle the second sample with one or more agents effective to hydrolyze entities which are hydrolyzed by urease for such a time and at a pH and at a temperature effective substantially to hydrolyze entities which are hydrolyzed by urease whereby the hydrolyzed sample is obtained commingled with the one or more agents, the hydrolysis system further comprising an agent separation and recovery element effective to separate the one or more agents from the hydrolyzed sample. This system may further comprise a carbon dioxide separation and recovery element for recovering carbon dioxide from the hydrolyzed sample commingled with the one or more agents. Additionally, the agent separation and recovery element may comprise a microporous membrane or an ultrafiltration membrane.

A preferred measuring system in accordance with this invention is specific to measuring carbon dioxide. More particularly, a preferred measuring system in accordance with this invention comprises a membrane having juxtaposed to one surface thereof a flow path for deionized water and juxtaposed to an opposite surface thereof a flow path for, alternatively, said first sample or said hydrolyzed sample, said measuring system further including a conductivity measuring element for measuring electrical conductivity of water in said flow path for deionized water after contact with said membrane. Another measuring system in accordance with this invention comprises a non-dispersive-infrared carbon dioxide photometer.

Apparatus in accordance with this invention may further include an estimating system for estimating total organic carbon and/or total carbon. More particularly, an estimating system in accordance with this invention estimates urea equivalent to a measure of carbon dioxide or total carbon dioxide, carbonic acid, bicarbonate and carbonate released by hydrolysis.

Methods for estimating as carbon dioxide the total of carbon dioxide, carbonic acid, bicarbonate and carbonate released by hydrolysis of hydrolyzable entities dissolved and/or dispersed in water containing such entities in accordance with this invention generally comprise the steps of:

(a) obtaining from a first sample of said water a measure of total concentration of carbon dioxide, carbonic acid, bicarbonate and carbonate in said sample before hydrolysis;

(b) hydrolyzing said hydrolyzable entities dissolved and/or dispersed in a second sample of said water whereby a hydrolyzed sample is obtained comprising carbon dioxide, carbonic acid, bicarbonate and/or carbonate and other hydrolysis products;

(c) obtaining from said hydrolyzed sample a measure of total concentration of carbon dioxide, carbonic acid, bicarbonate and carbonate in said hydrolyzed sample; and, (d) estimating from said measure of total concentration of carbon dioxide, carbonic acid, bicarbonate and carbonate in said first sample and from said total concentration of carbon dioxide, carbonic acid, bicarbonate and carbonate in said hydrolyzed sample, a measure as carbon dioxide of total carbon dioxide, carbonic acid, bicarbonate and carbonate released by hydrolysis of said hydrolyzable entities dissolved and/or dispersed in said water.

Methods according to this invention utilize one or more agents effective to hydrolyze entities which are hydrolyzed by urease, preferably utilizing urease, more preferably utilizing immobilized urease. In addition, methods according to this invention may utilize a membrane having juxtaposed to one surface thereof one or more hydrolytic agents effective to hydrolyze entities which are hydrolyzed by urease and having juxtaposed along another surface of said membrane a flow path for said second sample, said membrane being substantially impermeable to said one or more hydrolytic agents while being substantially permeable to urea and hydrolysis products thereof.

Methods according to this invention may also preferably utilize a membrane having juxtaposed to one surface thereof a flow path for deionized water and juxtaposed to an opposite surface thereof a flow path for, alternatively, said first sample or said hydrolyzed sample, and further comprising a step of measuring electrical conductivity of water in said flow path for deionized water after contact with said membrane. In a further embodiment, the membrane may be substantially impermeable to one or more agents effective to hydrolyze entities which are hydrolyzed by urease while being substantially permeable to water, carbon dioxide, carbonic acid, bicarbonate and carbonate.

BRIEF DESCRIPTIONS OF THE DRAWINGS

DETAILED DESCRIPTION OF PREFERRED EMBODIMENTS

Figure 1:
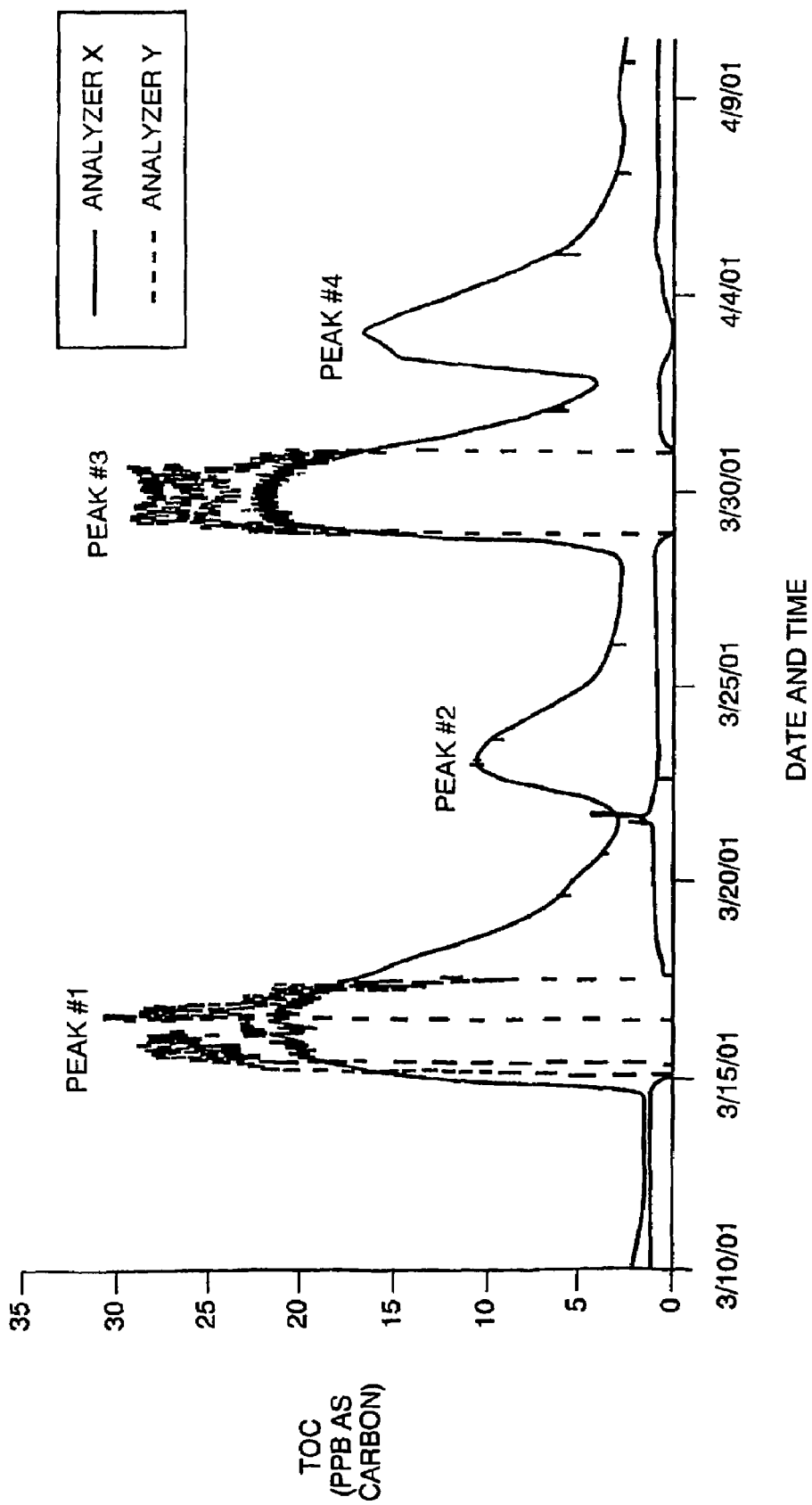
FIG. 1 is a graph of TOC measurements of four separate excursions over the period Mar. 10, 2001 to Apr. 9, 2001 using two different TOC analyzers.

As modern industrial processes, particularly in connection with semiconductor manufacture, require increasingly pure ultrapure water (UPW), it becomes a greater challenge accurately to measure actual contaminants without either measuring instrument noise or inadvertently contaminating ultrapure samples through handling while performing standard analytical laboratory techniques. Prior to this invention, there were no readily available laboratory methods or apparatus accurately to measure urea and related compounds at very low levels. Analytical techniques that did exist were not able to measure directly urea concentration; instead they measured total nitrogen content of a sample.

A. The Need to Detect Organic Nitrogen Compounds

It has recently become apparent that an urgent need exists for detecting very low levels of certain organic nitrogen compounds, specifically urea, in water used for semiconductor fabrication. In March and April of 2001, semiconductor fabrication facilities of a major manufacturer of semiconductor products, which were connected to a municipal city water supply, experienced a series of sudden and mysterious total organic carbon (TOC) spikes (excursions) caused by an unidentified component in their respective ultrapure water (UPW) systems. Although TOC levels in feed water did not show significant variations above baseline, TOC concentrations in UPW polish loops continued to increase. At no time since the construction and startup of these UPW systems several years earlier had there been excursions as severe and persistent as those mentioned above. In previous years, there were TOC excursions of short duration resulting from the annual turning of local reservoirs, but these excursions were treatable by the conventional UPW system. During the excursions in the spring of 2001, however, all immediate efforts to remove TOC contamination from the UPW systems by adjusting system parameters failed. Compounding frustrations, conventional laboratory analytical methods proved inadequate to identify the specific source or cause of the TOC concentration at the parts-per-billion levels detected by conventional TOC measuring technology. The lack of an effective analytical method to detect the subject contaminants ultimately required the development of the detection and measurement methods and apparatus of this invention.

These TOC excursions were either not detected or not measured accurately with an industry standard TOC analyzer (prior art), but were eventually successfully measured with a new type of analyzer according to this invention. Conventional ultrapure water purification techniques were not able to remove the organics causing the TOC excursions; accordingly, attempts were made to identify the compound(s) causing these excursions. By understanding the technologies of how two different analyzers operate, it was possible to develop a short list of possible contaminating components. Analysis of trace levels of organics in the excursions according to this invention eventually showed that urea, believed to have originated from agricultural activities in the nearby watershed, was the major component in each of the excursions. Urea decomposes naturally into carbon dioxide and ammonia; and the latter by-product is widely known throughout the semiconductor industry to impact negatively the performance of acid-catalyzed, chemically-amplified photoresists which are used in today's deep UV (DUV) photolithography processes.

B. Comparing Detection Results Using Two Different Types of Analyzers

In trying to address the new excursion problem, two different types of analyzers were tested: (1) an industry-standard TOC analyzer (herein identified as Analyzer Y), and (2) a Sievers Instruments TOC analyzer modified according to this invention (herein identified as Analyzer X). Both Analyzers X and Y as tested are reagentless analyzers which use high-intensity ultraviolet light to oxidize TOC into carbon dioxide, and use algorithms to convert calculated changes in electrical conductivity of an aqueous solution into a TOC concentration. In a conventional TOC determination, after a UV oxidation step in Analyzer X, carbon dioxide formed during oxidation of TOC is separated from the oxidized sample by means of a $CO_2$-selective membrane. Only carbon dioxide permeates the membrane and blends with a portion of sample that was not exposed to UV light. The conductivity of unexposed sample that accepted carbon dioxide is measured, and then compared to conductivity of an original, un-oxidized sample. Thus, in Analyzer X, the only contributor to the difference in conductivity is carbon dioxide.

Similar to Analyzer X, Analyzer Y, which has been an industry-standard analyzer for fifteen years, measures and compares pre- and post-oxidation conductivities of the sample exposed to high intensity UV light. Unlike Analyzer X however, Analyzer Y does not use a membrane to segregate carbon dioxide. In Analyzer Y, species contributing to changes in conductivity are not only carbon dioxide but also other oxidation byproducts that may be present.

Instead of recording similar results based on increased TOC levels in the UPW polish loops, as one skilled in this art might have expected, surprisingly the two types of analyzers reported very different results. Although Analyzer X and Analyzer Y each responded differently to the excursions, each played a role in helping to identify the component that caused the excursions. Analyzer X provided signal stability, accuracy, and was sensitive enough to detect the start of the excursions well before Analyzer Y. On the other hand, it was the characteristic lack of response of Analyzer Y to nitrogen-containing organics at concentrations less than 10 ppb that proved to be the primary clue to identifying the contaminant causing the new excursions.

C. The Test Results—Identifying the Contaminant

The test results are best understood in conjunction with the various figures. TOC data collected from one of the affected UPW systems, showing the differing results of the two different TOC analyzers, is shown in FIG. 1. The solid curve corresponds to the response of Analyzer X, while the dotted curve corresponds to the response of Analyzer Y during the excursions. FIG. 1 shows that Analyzer Y technology failed to detect any signal from two of the four TOC peaks, while Analyzer X responded to all of the peaks. Similar results were obtained in other tests at other factories that were exposed to the same feed water. At the affected sites, Analyzer Y provided readings that varied between near zero to levels exceeding 150 ppb.

Figure 2:
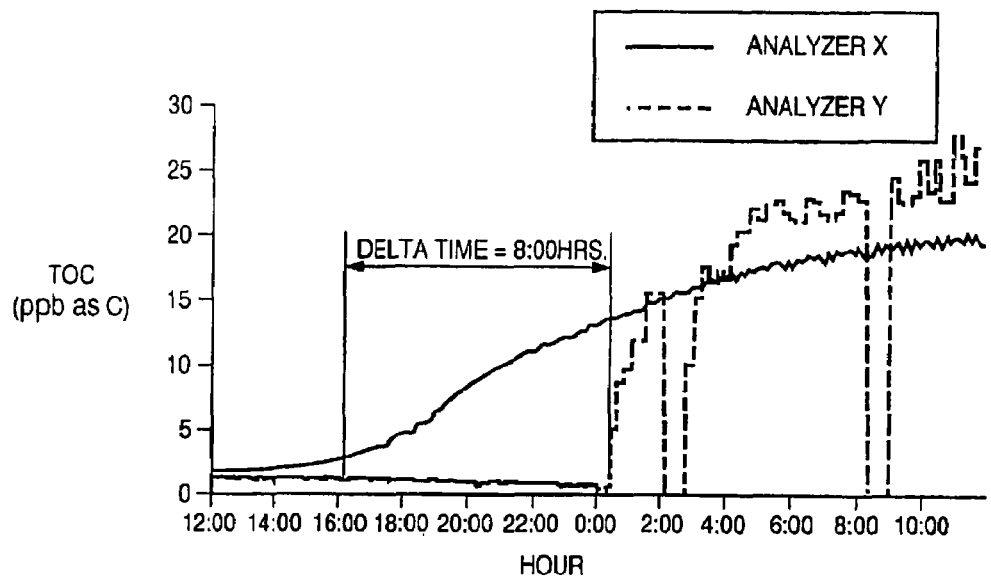
FIG. 2 is a close up of the spike caused by the first excursion.

FIG. 2 shows a detailed observation of the start of the first excursion as seen in FIG. 1. A study of this detail provided clues to the identification of the compound(s) causing the TOC excursions. Analyzer X responded about 8 hours in advance of Analyzer Y. One important point to note here is that the curve for Analyzer Y approached zero as the amount of contaminant increased (as measured by Analyzer X). Only after the TOC contaminant reached a concentration of approximately 15 ppb did Analyzer Y recognize the presence of the contaminant, and even then produced the erratic results shown in FIGS. 1 and 2.

Figure 3:
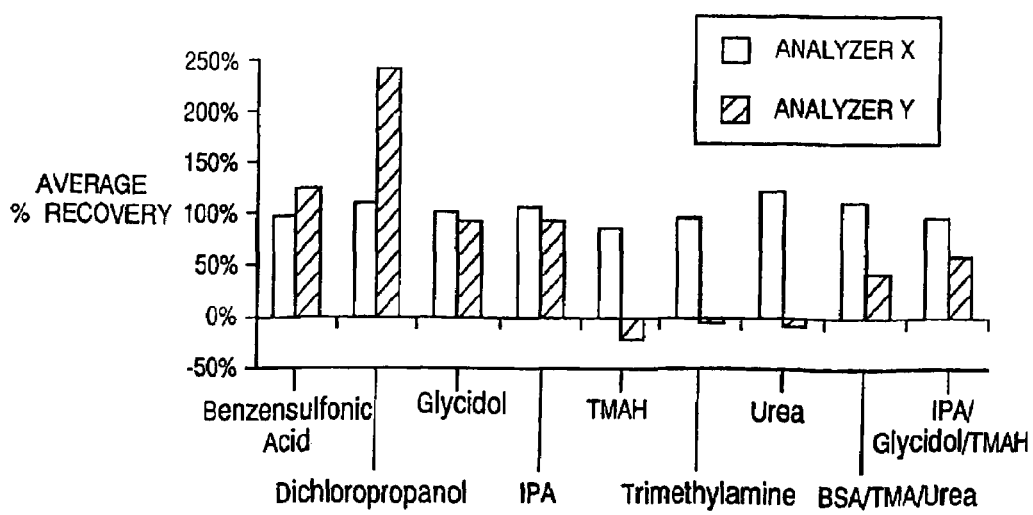
FIG. 3 is a bar graph showing average recovery (detection) of different contaminants using two different analyzers.

In another set of tests, the performance characteristics of different UPW TOC analyzers were evaluated in detecting various types of organic compounds, the results of which are shown in FIG. 3. For this study, measured amounts ranging from 0.03 ppb to 5 ppb (as carbon) of various organic compounds that were thought to have the potential to contaminate UPW were added to UPW streams. FIG. 3 shows that Analyzer Y did not respond to urea, trimethylamine, or tetramethylammonium hydroxide (TMAH), each of these being a nitrogen-containing carbon compound. By contrast, Analyzer X provided close to 100 percent detection and measurement (based on the actual amounts added) of these organic nitrogen compounds. Therefore, given the response of Analyzer X and Analyzer Y during the TOC excursions, as discussed above relative to FIG. 1, it was concluded that the contaminant was probably a nitrogen-containing carbon compound. It still remained to be determined which compound or compounds caused the excursion.

Trimethylamine is a chemical functional group decomposed from the anion exchange resin used in the UPW system. With its positive charge, such resin attracts and removes negatively charged ions from UPW. Trimethylamine would be expected to originate from decomposing anion exchange resin and impact a single facility, but the subject TOC excursions occurred simultaneously at three different company factories as well as at several other semiconductor manufacturing facilities of other companies using the same municipal water supply. Also, one facility that had the capability of changing city water sources was able to switch their water sourcing between the third and fourth excursions, and, as a result, was not impacted by the fourth excursion. These data suggested that the problem contaminant was probably not trimethylamine.

Tetramethylammonium hydroxide (TMAH) is commonly used as a developer during photolithography processing steps. However, it is unlikely that TMAH was the source of contamination because the repeated excursions experienced by several semiconductor manufacturers using city water pointed to a contaminant in the city water supply. There are no known industries in the area watershed that discharge TMAH to the water supply.

Urea is a commonly used fertilizer, and could very well be present in the city water as a result of rainwater runoff into streams and rivers from which the city water is sourced. The area where the plants are located is primarily agricultural. A mass balance at one facility showed that, depending on the percent of rejection of contaminant by the reverse osmosis arrays, between 100 and 500 pounds of urea (approximately 0.006 percent of the almost 7 million pounds spread annually within the regional watershed) could have caused the first excursion shown in FIG. 1. It was also determined that the timing of the TOC excursions coincided with the start of the annual March-through-June fertilization cycle. Other reasons to suspect that urea was, in fact, the mystery contaminant included the facts that urea: (1) meets all the requirements to pass-through a modern UPW system; (2) is a naturally occurring organic decomposition product; (3) is commonly used in agriculture as a fertilizer; (4) could possibly contaminate the city water supply through farming and commercial activities; (5) is an organic nitrogen compound that Analyzer Y and comparable analyzers do not recover under 10-15 ppb as C; and, (6) other companies have looked at controlling urea in UPW.

D. Sensitive Detection of Urea and Related Compounds With the Apparatus and Methods of This Invention Common and familiar analytical techniques available to measure contaminants in UPW include Inductively Coupled Plasma-Mass Spectrometry (ICP/MS), Graphite Furnace Atomic Absorption Spectrometry (GFAAS), and Ion Chromatography (IC). ICP/MS and GFAAS can measure metal and organometallic contaminants to the sub ppb level, and IC can measure ions at similar concentrations. Until recently, however, there were no methods to detect nonionic, non-metallic organics that contained sulfur, nitrogen, or chlorine. In 1999, an analytical device was developed that combined UV oxidation with IC to measure organic-combined sulfate, chloride, and nitrate compounds to sub-ppb concentrations. Although this new technique would have been helpful in narrowing down the list of possible contaminants that caused the subject excursions to a broad family of compounds, however, it would not have been able to isolate and identify the specific contaminant.

Figure 4A:
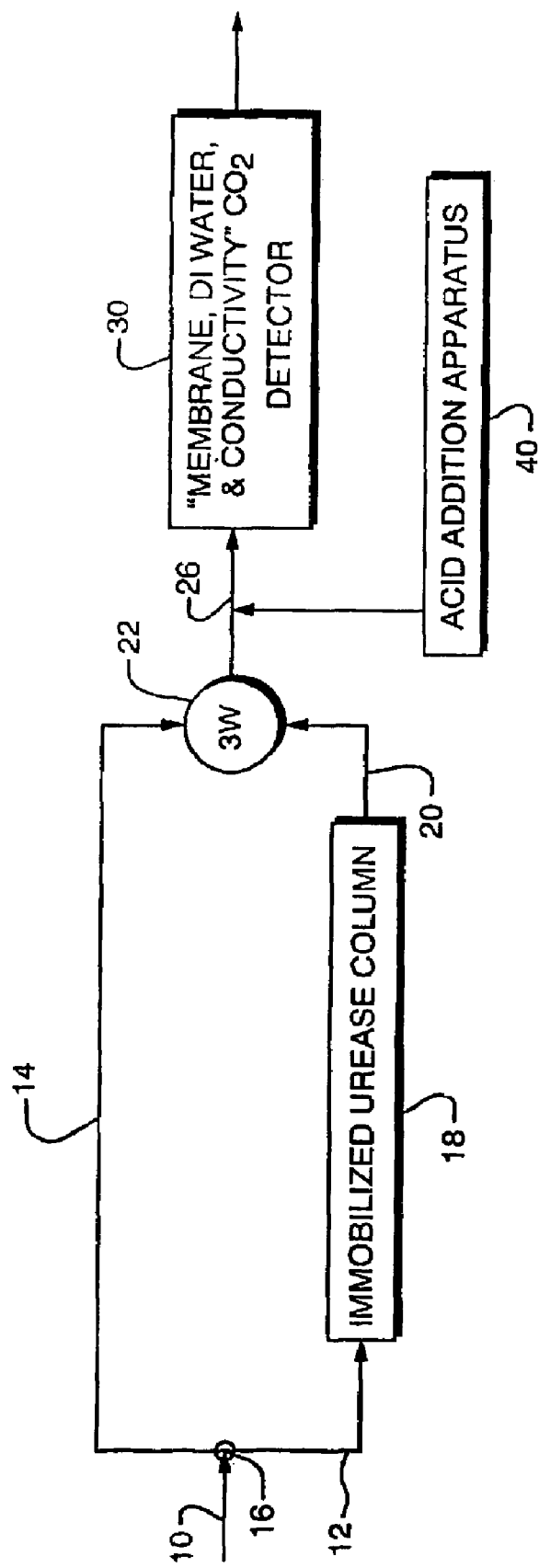
FIG. 4a is a schematic process flow chart illustrating a first system for sensitive detection of urea and other compounds hydrolysable to carbon dioxide group compounds according to the present invention.

To confirm that urea was the cause of the subject excursions, and to establish apparatus and methods for detecting similar excursions in the future, an on-line, urea-specific analyzer in accordance with this invention was developed and tested. A schematic process flow diagram illustrating a first preferred embodiment of apparatus for sensitive detection of organic nitrogen compounds, particularly urea, in accordance with this invention is shown in FIG. 4a. As seen in FIG. 4a, an initial stream of water to be analyzed, e.g., an UPW stream used in semiconductor fabrication, carried in an analysis inlet conduit 10, is divided into first and second analysis streams, carried respectively in treatment conduit 12 and bypass conduit 14, by a fluid divider 16, which may comprise a valve member, a simple T-junction or Y-junction, or other fluid divider element.

The first analysis stream in conduit 12 is passed into contact with a catalyst such as urease, for example in an immobilized urease column 18, which substantially and reproducibly hydrolyzes any urea in the first analysis stream to carbon dioxide and ammonia according to the equation:

$$\text{Urea} \xrightarrow{\text{urease}} CO_2 + 2\,NH_3$$

The $CO_2$ may be present as any one or more of the members of the carbon dioxide group and the $NH_3$ as $NH_3$ or $NH_4^+$ depending upon the pH, the temperature and the relevant equilibria.

The water stream emerging from hydrolysis column 18 is a treated water stream carried by outlet conduit 20 to one branch of 3-way valve 22 or similar fluid flow control element. Bypass conduit 14 carries untreated water from fluid divider 16 to a second branch of 3-way valve 22. Depending on the adjustable valve control setting for valve 22, either a treated water stream from conduit 20 or an untreated water stream from conduit 12 is alternatively passed through valve 22 to detector inlet conduit 26 for analysis in detector 30.

Detector inlet conduit 26 conveys the water stream from valve 22 into low-level $CO_2$ detector 30 which may be part of a Total Organic Carbon ("TOC"), Total Inorganic Carbon ("TIC") and/or Total Carbon ("TC") analyzer. Detector 30 in FIG. 4a preferably comprises a two-compartment $CO_2$ sensor, similar to that taught in U.S. Pat. No. 5,132,094, wherein the two fluid compartments are separated by a $CO_2$-selective membrane, such as a PFA (perfluoroalkoxy resin) membrane.

As taught in the Godec et al. '094 patent, a water stream to be analyzed is flowed into, through, and out of a first fluid compartment of the $CO_2$ sensor, while a second water stream, e.g., a deionized (DI) water stream, is flowed through the second fluid compartment of the sensor. At least a portion of the carbon dioxide in the water stream flowing through the first compartment diffuses across the $CO_2$-selective membrane and into the DI water stream flowing through the second compartment, thereby changing the conductivity of that DI water stream. Changes in the conductivity of the DI water stream during analysis of treated water, relative to the conductivity change during analysis of untreated water, can be mathematically correlated with the carbon dioxide group content of the fluid stream in the first compartment and, in turn, with the concentration of urea in the UPW. If detector 30 includes a UV lamp, such as that in a TOC and/or TC analyzer, the UV lamp is preferably turned off for analyses in accordance with the present invention.

The water stream in or from conduit 26 is acidified and/or acid buffered, for example by the addition of phosphoric acid, from acid addition source 40 prior to being passed to the first fluid compartment of detector 30. The phosphoric acid and/or acidic buffer converts ammonia in treated water coming from urease column 18 into ammonium ions, and these ions are blocked by the $CO_2$-selective membrane from diffusing into the DI water stream in the second compartment of detector 30. Such acid or acidic buffer also converts carbon dioxide group compounds substantially and reproducibly to $CO_2$ per se. Preferably such acid and/or acidic buffer results in a pH which is substantially reproducible, predetermined and substantially less than the pK corresponding to the conventional or practical first ionization constant of carbonic acid. Accordingly, any increased change in the conductivity of the DI water stream during the analysis of the treated water stream, relative to the change in the conductivity of the DI water stream during analysis of the untreated water stream, must be accounted for by the increased presence of carbon dioxide group compounds in the treated water stream. In turn, the increased presence of carbon dixoide group compounds in the treated water stream in conduit 20 coming from hydrolysis column 18 must be due to the presence of urea in the initial UPW stream in conduit 10, which urea was converted to $CO_2$ and $NH_3$ and related compounds in column 18.

Although the detection system illustrated in FIG. 4a and discussed above is specific with respect to urea detection, in accordance with further embodiments of this invention that detection system may be adapted for the low-level detection of other related compounds. There are known catalysts, e.g., enzymes, which can be substituted for urease for promoting enzymatic decomposition of other compounds into carbon dioxide group compounds. The remainder of the detection system shown in FIG. 4a, in particular the design and operation of detector 30, would be substantially the same as or identical to that as discussed above.

Figure 4B:
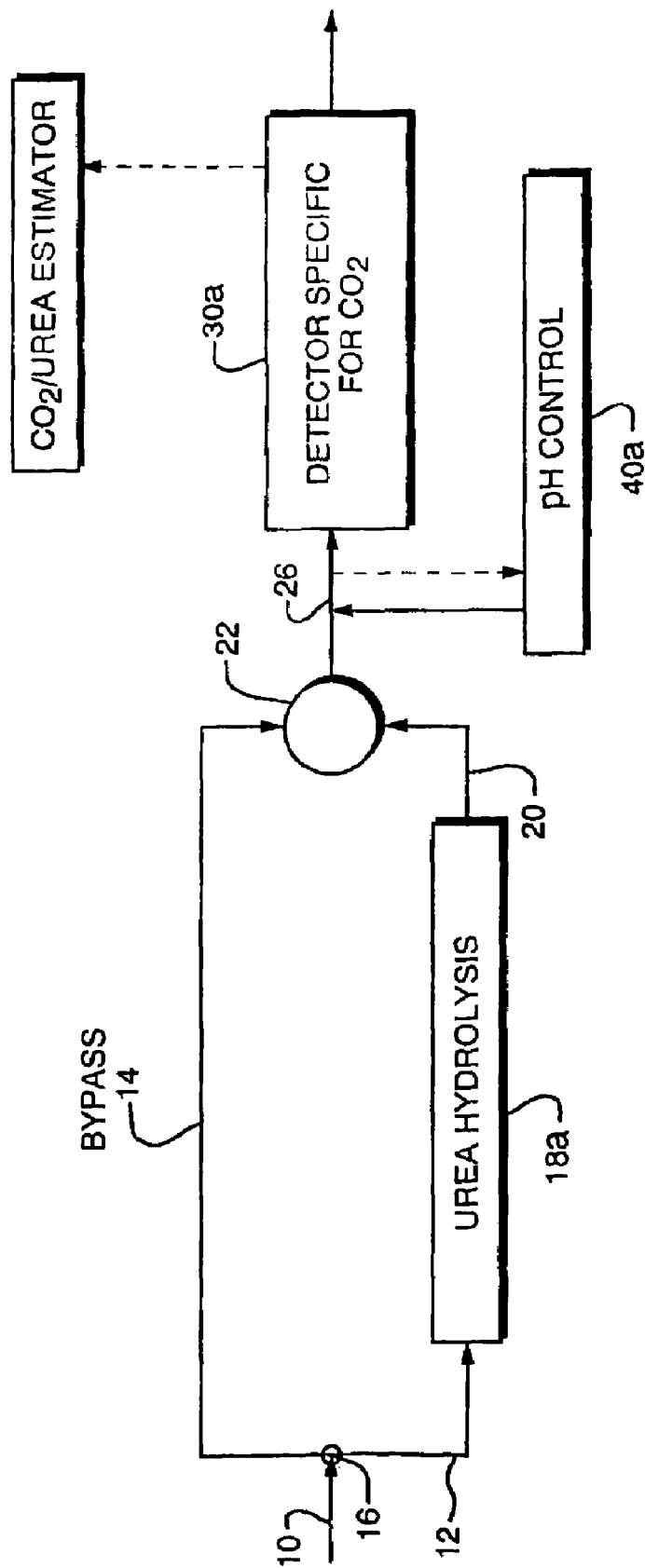
FIGS. 4b, 4c and 4d are schematic process flow charts illustrating other preferred systems for sensitive detection of urea and other compounds hydrolysable to carbon dioxide group compounds in accordance with this invention.
Figure 4C:
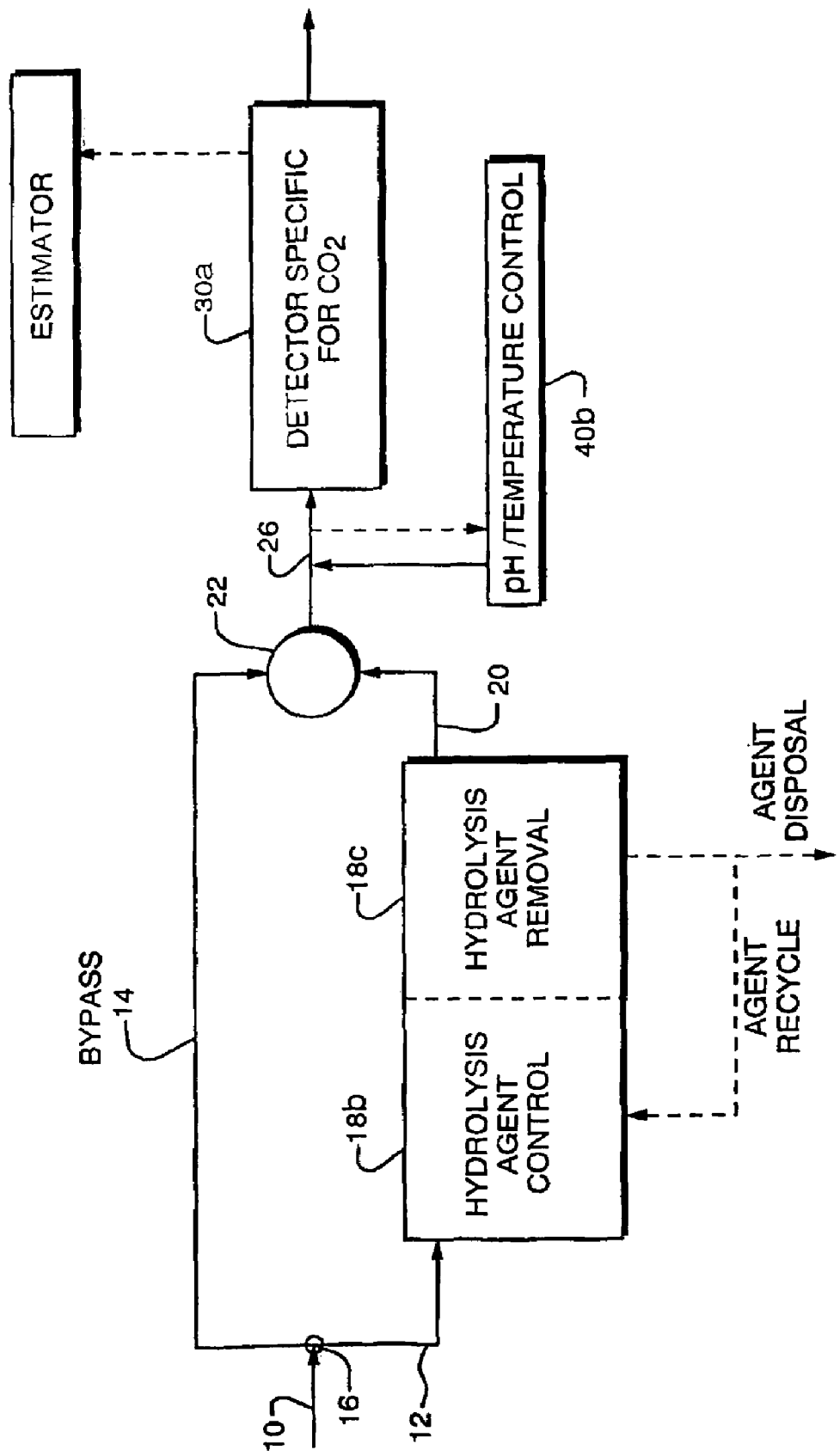
Figure 4D:
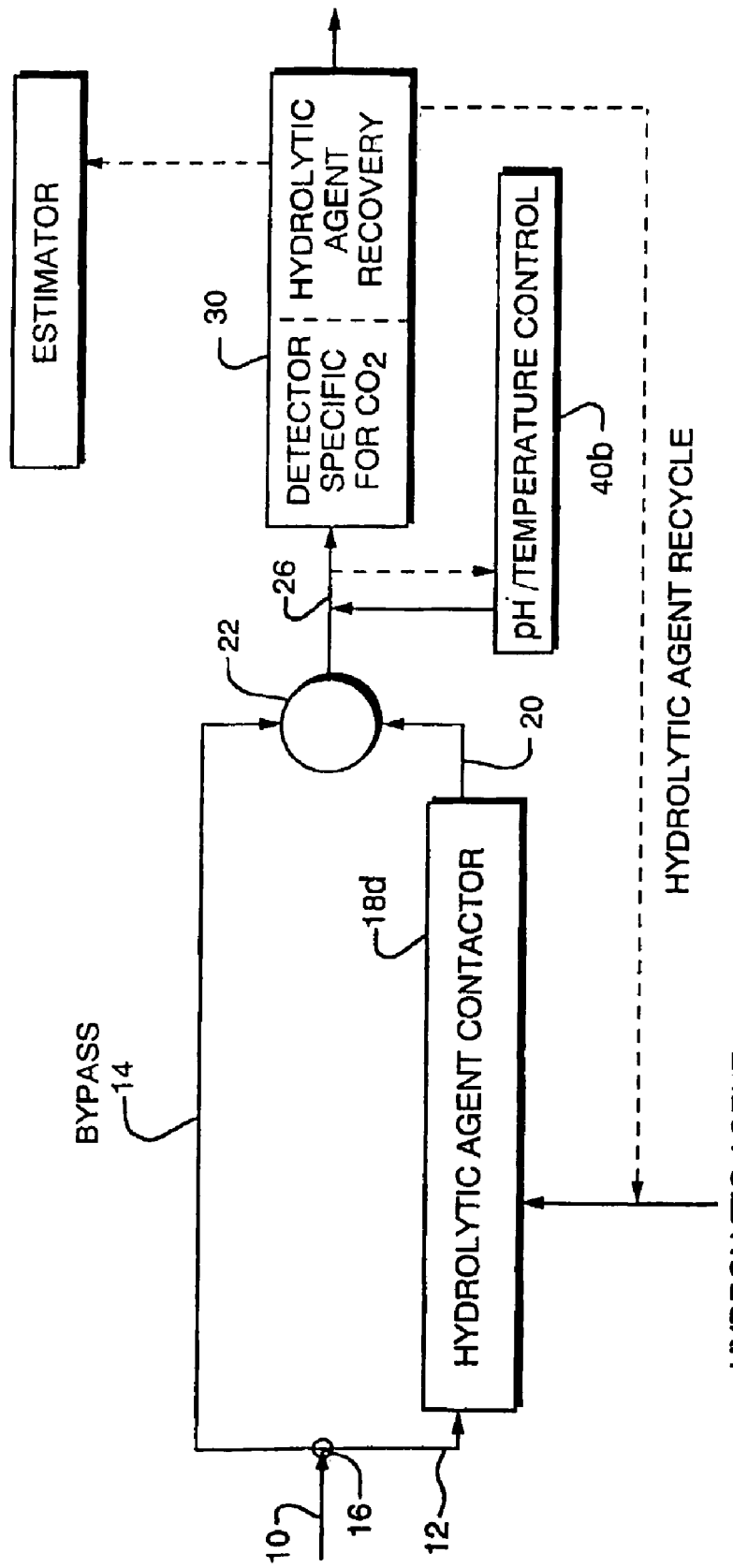

FIGS. 4b, 4c and 4d illustrate additional preferred embodiments of the methods and apparatus of the invention. Numbers in FIGS. 4a, 4b, 4c and 4d generally refer to similar apparatus or process elements. The process flow diagram of FIG. 4b includes a $CO_2$/urea estimator, calculator, program, or algorithm associated with detector 30a (as indicated by the dotted arrow) for converting measures of $CO_2$ from detector 30a, a "Detector Specific for $CO_2$," into estimates of $CO_2$ and/or urea in water sampled. Also included are an optional pH control system 40a which may include a pH sensor for sensing the pH of fluid in conduit 26 and, responsive thereto (as indicated by the dotted arrow), an addition element for adding an acidic buffer and/or a suitable acid as needed. Depending upon the detector, the nature of the water sampled, and the urea hydrolysis system 8a, such pH control system 40a may not be required or the pH sensor in system 40a may not be required, it being sufficient to add a predetermined amount of acid or acidic buffer to the sample. Urea hydrolysis system 18a may or may not include urease, but generally will include at least some hydrolytic/hydrolysis agent or agents. The latter may be immobilized, for example, on macroporous beads or other structures, confined by microporous or ultra filtration membranes impermeable to the agent or agents but permeable to urease and related compounds and to their hydrolysis products. Such membrane or membranes may be in the form of spaghetti, solid fine fibers or hollow fine fibers, or as films or sheets covering a thin, narrow tortuous path.

According to the embodiment of FIG. 4c, a hydrolytic agent or agents, which may be or may include urease, is commingled with the second sample (the first sample being that flowing through bypass 14), and the hydrolyzed sample and hydrolysis agents or agent are separated, e.g., by porous membranes, gravity settling or the like, in a hydrolysis agent separation and recovery system. The hydrolytic agent(s) thus recovered may optionally be sent to disposal, recycled in whole or in part, or both. The optional pH control system 40b (comparable to 40a in FIG. 4b) may also optionally include a temperature control element. Such systems may also optionally include a carbon dioxide separation and recovery element for recovering carbon dioxide from the hydrolyzed sample commingled with the one or more hydrolysis agents.

In accordance with FIG. 4d, a hydrolytic agent or agents, which may include or may be urease, is fed to the hydrolytic agent contactor 18d where it is commingled with the second sample; and, the mixture, at an appropriate pH and temperature and after a time sufficient to achieve sufficient hydrolysis, is sent to a $CO_2$ specific detector. Thereafter, optionally the agent or agents and hydrolyzed sample may be separated in a hydrolytic agent separation and recovery system. The agent or agents optionally can be recycled.

Long research was conducted to demonstrate that an analyzer constructed and operated in accordance with the present invention produced highly accurate detection of urea in water at levels ranging from about 100 ppb of urea (as C) down to extremely low levels of about 0.10-0.15 ppb of urea (as C), and that the analyzer of this invention (Analyzer X) performed far more reliably than the previous industry standard (Analyzer Y). Thus., a prototype urea analyzer was tested at levels of urea concentrations similar to the TOC levels observed during the subject excursions.

Figure 5:
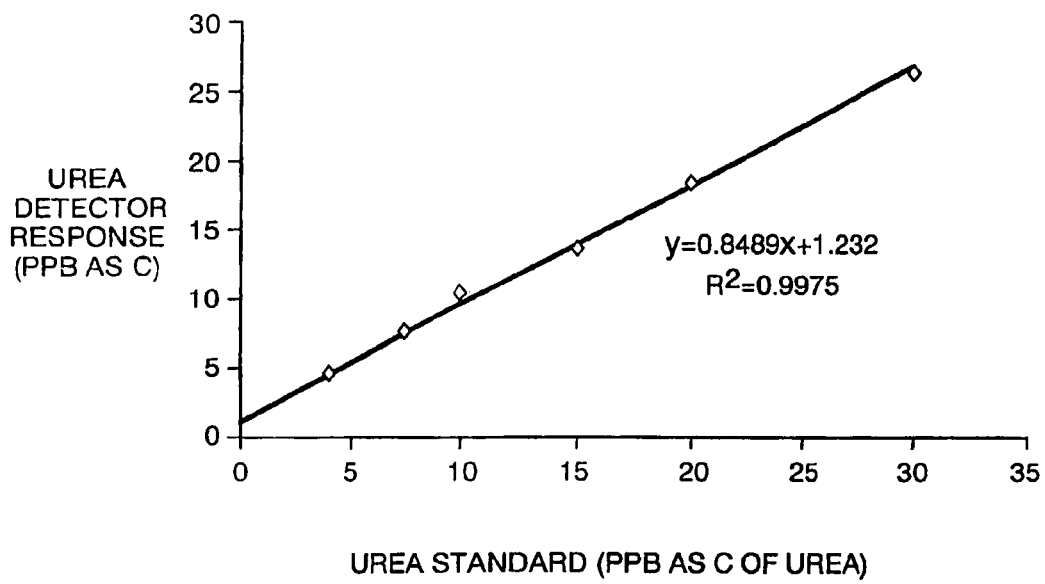
FIG. 5 is a graph illustrating the accuracy and responsiveness of an analyzer of the present invention in a high-range calibration.
Figure 6:
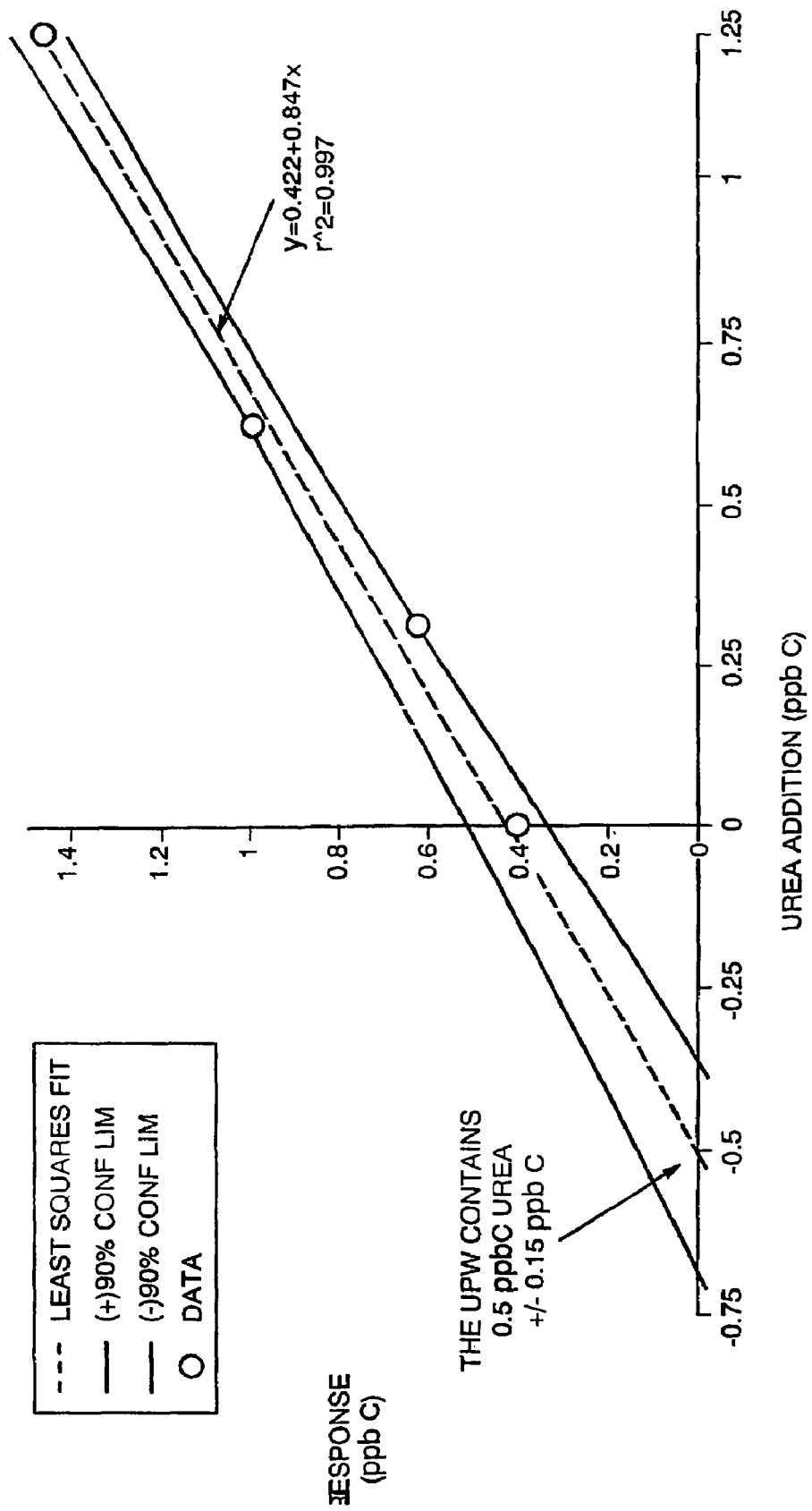
FIG. 6 is a graph illustrating the accuracy and responsiveness of an analyzer of the present invention in a low-range calibration.
Figure 7:
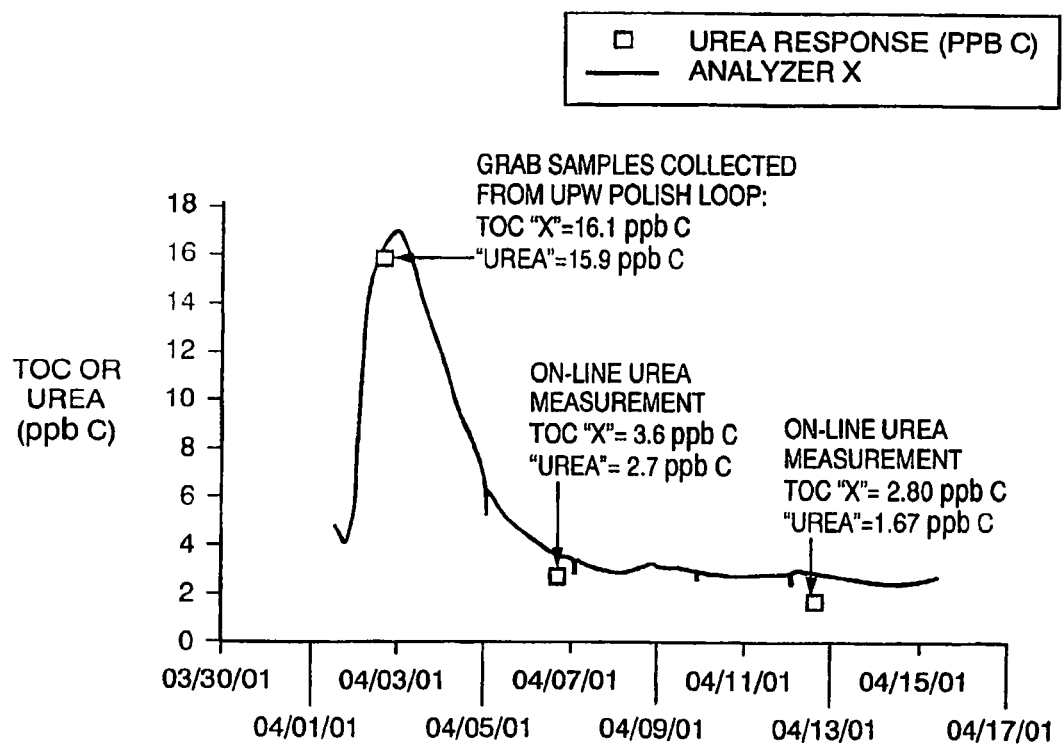
FIG. 7 is a graph showing a correlation between measured urea concentration and TOC concentration for the fourth excursion using an analyzer of the present invention.

In a high-range calibration of an analyzer according to this invention, carried out using standard solutions of urea ranging from about 5 ppb of urea (as C) up to about 35 ppb of urea (as C), as seen in FIG. 5, Analyzer X, modified to operate in accordance with this invention, recovered urea at a constant 85 percent during initial calibration with standard solutions. In a low-range calibration of an analyzer according to the present invention, carried out using standard solutions of urea ranging from about 0.10 ppb of urea (as C) up to about 1.25 ppb of urea (as C), as seen in FIG. 6, Analyzer X (as modified) again detected urea at a high degree of accuracy. Using refrigerated and sealed grab samples from the fourth excursion as previously discussed, Analyzer X (as modified) was able to identify correctly that urea, as shown in FIG. 7, was the primary cause of the fourth excursion.

Figure 8:
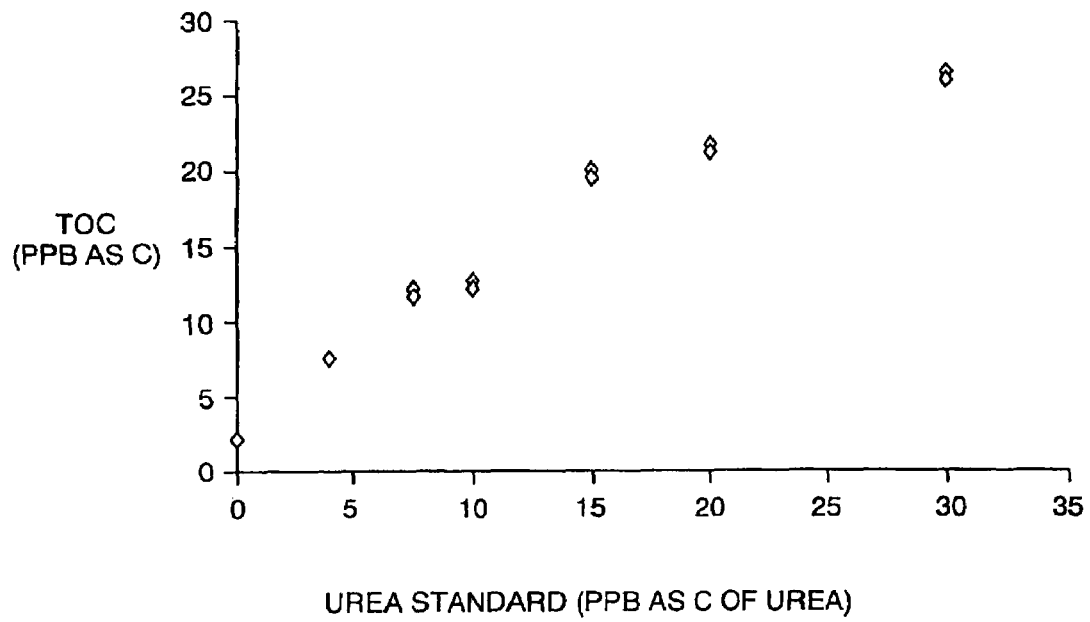
FIGS. 8 and 9 are graphs comparing the respective responsiveness to urea of two analyzers, one according to the present invention (FIG. 8), the other representing a prior art instrument (FIG. 9).

To compare further the performance of Analyzers X (as modified) and Y in detecting low-level urea contamination, standard addition tests using various concentrations of urea were conducted. The responses of both Analyzers X (FIG. 8) and Y (FIG. 9) in the controlled laboratory environment corresponded well to the real-time results obtained for the first excursion as seen in FIG. 2. This data appears to confirm that urea was responsible for the first and subsequent excursions shown in FIG. 1, as well as the fourth excursion shown in FIG. 7.

Figure 9:
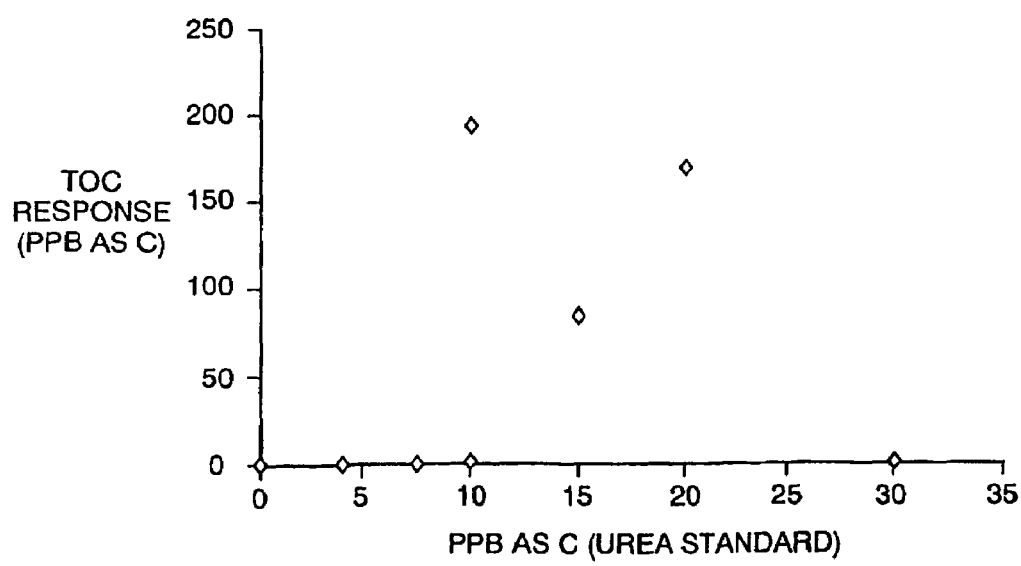

One notable aspect of FIG. 9 is the extent of the overreaction of Analyzer Y to urea concentrations greater than 10 ppb. As noted above, both Analyzer X and Analyzer Y each use algorithms to convert conductivity differences resulting from TOC concentration. However, Analyzer X measures only conductivity change caused by creation of carbon dioxide, while Analyzer Y measures overall conductivity change of a sample, which could be a result of components other than carbon dioxide. It is believed that when urea is oxidized with UV light, in accordance with the method of Analyzer Y, some urea is oxidized into nitric acid. Therefore, it is believed that the overreaction by Analyzer Y may result because the conductivity differential measured by Analyzer Y is caused by more than just carbon dioxide. Because Analyzer X, constructed and operated according to the present invention, uses a $CO_2$ specific detector, such as a detector which includes a $CO_2$-selective membrane, which segregates a measured conductivity difference from extraneous chemical reactions, it provides more accurate and more stable measurements for urea, like those shown in FIG. 8.

A possible limitation on the use of the present invention sensitively to detect low levels of urea may be the presence in the UPW of competitive substrates, such as N,N-dimethyl urea and ethylurea, which may react with urease in the same way as does urea. Such competitive substrates, however, are not typically found in UPW. Another possible limitation may be the presence of substances, such as N-methyl pyrrolidone (NMP), N-(n-butyl) thiophosphoric triamide (NBPT), boric acid, hydroquinone, fluorofumide, and thioglycolic acid. However, there are no natural sources of these materials in high enough concentrations to cause trouble, and they would typically be removed by normal water purification systems.

Figure 10:
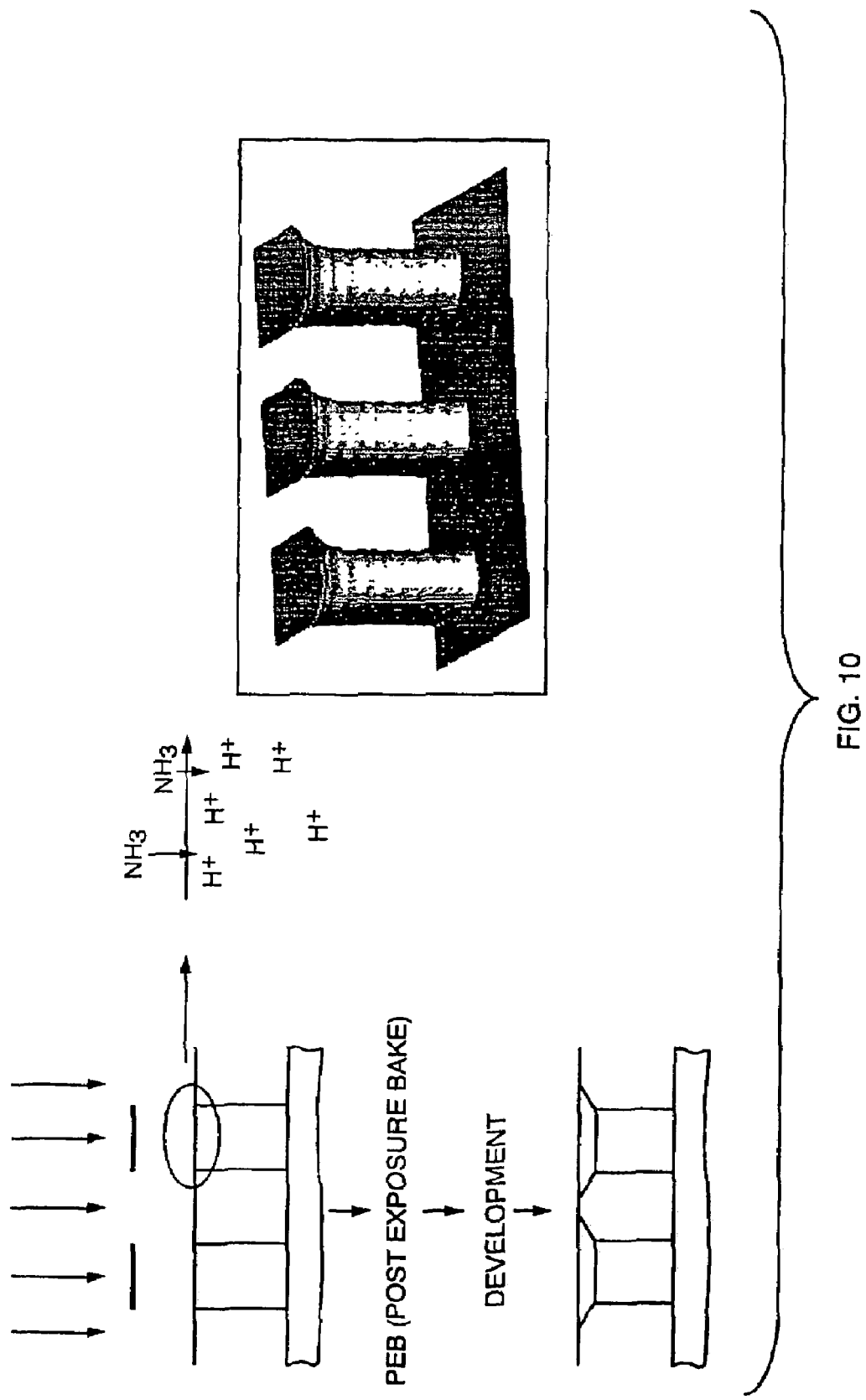
FIG. 10 is a schematic illustration of the so-called T-topping effect caused by ammonia contamination of the fab in a semiconductor plant.

With the advances in acid-catalyzed, chemically-amplified photoresists used in today's deep TV photolithography processes come new sensitivities to the ambient environment. There are many ways that ultrapure water can get into the fab or lithography tool atmosphere, e.g., through humidification processes or water rinsing processes. The negative effects of low concentrations of airborne molecular contaminants, such as low or sub-ppb levels of organic amines and ammonia, on the control of critical dimensions during the lithography of sub-0.5-μm linewidths is widely known throughout in the semiconductor industry, as discussed for example in the following cited literature references, and is illustrated in FIG. 10. See, e.g., W. Henke, "Simulation for DUV—Lithography", Semiconductor Fabtech 9th Ed., Section 5 Lithography, March 1999, page 211-218; S. A. MacDonald et al., "Airborne Chemical Contamination of a Chemically Amplified Resist," in Proceedings of Advances in Resist Technology and Processing VIII (Bellingham, Wash.: International Society for Optical Engineering [SPIE], 1991), 1-12; J. C. Vigil, M. W. Barrick, and T. H. Grafe, "Contamination Control for Processing DUV Chemically Amplified Photoresists," in Proceedings of SPIE's International Symposium on Microlithography (Bellingham, Wash.: SPIE, 1995), 210; and, Z. Lin and A. F. VanNatter "using CD SEM to Evaluate Material Compatibility with DUV Photoresists," http://www.micromagazine.com/archive/99/02/lin.html. Accordingly, sensitive detection of urea and related compounds in accordance with the present invention can also prevent contamination of semiconductor fabrication environments and thereby dramatically improve the quality and performance of photoresists and other semiconductor products fabricated in those environments.

It will be apparent to those skilled in the art that other changes and modifications may be made in the above-described apparatus and methods for low level detection and measurement of organic nitrogen compounds without departing from the scope of the invention herein, and it is intended that all matter contained in the above description shall be interpreted in an illustrative and not a limiting sense.

The invention claimed is:

1. Apparatus for estimating a measure as carbon dioxide of the total of carbon dioxide, carbonic acid, bicarbonate and carbonate released by hydrolysis of hydrolyzable entities dissolved and/or dispersed in water containing such entities based on comparison of a carbon dioxide measurement on a sample of said water before hydrolysis with a carbon dioxide measurement on a sample of said water after hydrolysis, such apparatus comprising:

(a) a measuring system for obtaining a first measure of total concentration of carbon dioxide, carbonic acid, bicarbonate and carbonate using a sample of said water before hydrolysis, wherein said measuring system comprises in combination: (i) a $CO_2$-selective measuring system membrane having juxtaposed to one surface thereof a flow path for deionized water; (ii) the membrane also having juxtaposed to an opposite surface thereof a flow path for said sample of water before hydrolysis; and, (iii) a conductivity measuring element for measuring electrical conductivity of water in said flow path for deionized water downstream of said measuring system membrane;

(b) a hydrolysis system effective substantially to hydrolyze said hydrolyzable entities dissolved and/or dispersed in a sample of said water whereby a hydrolyzed sample is obtained comprising carbon dioxide, carbonic acid, bicarbonate and/or carbonate and other hydrolysis products;

(c) a measuring system for obtaining a second measure of total concentration of carbon dioxide, carbonic acid, bicarbonate and carbonate using said hydrolyzed sample wherein said measuring system comprises in combination: (i) a $CO_2$-selective measuring system membrane having juxtaposed to one surface thereof a flow path for deionized water; (ii) the membrane also having juxtaposed to an opposite surface thereof a flow path for said hydrolyzed sample; and, (iii) a conductivity measuring element for measuring electrical conductivity of water in said flow path for deionized water downstream of said measuring system membrane; and, (d) an estimating system for estimating from said first and second measures of total concentration of carbon dioxide, carbonic acid, bicarbonate and carbonate a measure as carbon dioxide of total carbon dioxide, carbonic acid, bicarbonate and carbonate released by hydrolysis of said hydrolyzable entities dissolved and/or dispersed in said water.

2. Apparatus according to claim 1 wherein said hydrolysis system comprises one or more agents effective to hydrolyze entities which are hydrolyzed by urease.

3. Apparatus according to claim 1 wherein said hydrolysis system comprises urease.

4. Apparatus according to claim 1 wherein said hydrolysis system comprises immobilized urease.

5. Apparatus according to claim 1 wherein said hydrolysis system comprises a hydrolysis system membrane having juxtaposed to one surface thereof one or more hydrolytic agents effective to hydrolyze entities which are hydrolyzed by urease and also having juxtaposed along another surface of said membrane a flow path for the sample being hydrolyzed, said hydrolysis system membrane being substantially impermeable to said one or more hydrolytic agents while also being substantially permeable to urea and to urea hydrolysis products.

6. Apparatus according to claim 5 further wherein one or more of said hydrolytic agents consist essentially of urease.

7. Apparatus according to claim 1 wherein said measuring system obtains at an acidic pH said measure of total concentration of carbon dioxide, carbonic acid, bicarbonate and carbonate in said sample of water before hydrolysis or, alternatively, of said hydrolyzed sample.

8. Apparatus according to claim 1 wherein said apparatus further includes an estimating system for estimating total organic carbon and/or total carbon.

9. Apparatus according to claim 1 wherein the measuring system that measures said sample of said water before hydrolysis is also the measuring system that measures said hydrolyzed sample.

10. Apparatus according to claim 5 wherein the measuring system that measures said sample of said water before hydrolysis alternatively serves as the measuring system that measures said hydrolyzed sample.

11. Apparatus according to claim 1 wherein said sample of said water before hydrolysis is hydrolyzed to become said hydrolyzed sample.

12. Apparatus according to claim 1 wherein said estimating system estimates urea equivalent to said measure as carbon dioxide of total carbon dioxide, carbonic acid, bicarbonate and carbonate released by hydrolysis.

13. Apparatus according to claim 1 wherein a measuring system obtains, at a pH numerically less than the conventional pK corresponding to the first ionization constant of carbonic acid, said measure as carbon dioxide of total concentration of carbon dioxide, carbonic acid, bicarbonate and carbonate in a sample of said water before hydrolysis or a hydrolyzed sample.

14. Apparatus according to claim 1 wherein said hydrolysis system comprises a hydrolysis system membrane substantially impermeable to one or more agents effective to hydrolyze entities which are hydrolyzed by urease while also being substantially permeable to water, carbon dioxide, carbonic acid, bicarbonate and carbonate.

15. Apparatus according to claim 1 wherein said hydrolysis system comprises a mixing and contacting element to commingle a sample of said water with one or more agents effective to hydrolyze entities which are hydrolyzed by urease for such a time and at a pH and at a temperature effective substantially to hydrolyze entities which are hydrolyzed by urease to form said hydrolyzed sample commingled with said one or more agents, said hydrolysis system further comprising an agent separation and recovery element effective to separate said one or more agents from said hydrolyzed sample.

16. Apparatus according to claim 1 wherein said hydrolysis system comprises a mixing and contacting element to commingle a sample of said water with one or more agents effective to hydrolyze entities which are hydrolyzed by urease for such a time and at a pH and at a temperature effective substantially to hydrolyze entities which are hydrolyzed by urease to form said hydrolyzed sample commingled with said one or more agents, said apparatus further comprising a carbon dioxide separation and recovery element for recovering carbon dioxide from said hydrolyzed sample commingled with said one or more agents.

17. Apparatus according to claim 15 wherein said agent separation and recovery element comprises a microporous membrane or an ultrafiltration membrane.

18. Apparatus according to claim 16 wherein said apparatus further includes an agent separation and recovery element effective to recover said one or more agents.

19. A method for estimating a measure as carbon dioxide of the total of carbon dioxide, carbonic acid, bicarbonate and carbonate released by hydrolysis of hydrolyzable entities dissolved and/or dispersed in water containing such entities based on comparison of a carbon dioxide measurement on a sample of said water before hydrolysis with a carbon dioxide measurement on a sample of said water after hydrolysis, said method comprising the steps of:

(a) obtaining a first measure of total concentration of carbon dioxide, carbonic acid, bicarbonate and carbonate using a sample of water before hydrolysis by contacting said sample of water before hydrolysis with a surface of a $CO_2$-selective measurement system membrane, the opposite surface of which is juxtaposed to a flow path carrying deionized water, and by measuring the electrical conductivity of water in said flow path carrying deionized water downstream of the measurement system membrane;

(b) hydrolyzing said hydrolyzable entities dissolved and/or dispersed in a sample of said water whereby a hydrolyzed sample is obtained comprising carbon dioxide, carbonic acid, bicarbonate and/or carbonate and other hydrolysis products;

(c) passing said hydrolyzed sample to a measurement system and then obtaining a second measure of total concentration of carbon dioxide, carbonic acid, bicarbonate and carbonate using said hydrolyzed sample by contacting said hydrolyzed sample with a surface of a $CO_2$-selective measurement system membrane, the opposite surface of which is juxtaposed to a flow path carrying deionized water, and by measuring the electrical conductivity of water in said flow path carrying deionized water downstream of the measurement system membrane; and, (d) estimating from said first and second measures of total concentration of carbon dioxide, carbonic acid, bicarbonate and carbonate a measure as carbon dioxide of total carbon dioxide, carbonic acid, bicarbonate and carbonate released by hydrolysis of said hydrolyzable entities dissolved and/or dispersed in said water.

20. A method according to claim 19 wherein step (b) utilizes one or more agents effective to hydrolyze entities which are hydrolyzed by urease.

21. A method according to claim 19 wherein step (b) utilizes urease.

22. A method according to claim 19 wherein step (b) utilizes immobilized urease.

23. A method according to claim 19 wherein step (b) utilizes a hydrolysis system membrane having juxtaposed to one surface thereof one or more hydrolytic agents effective to hydrolyze entities which are hydrolyzed by urease and also having juxtaposed along another surface of said membrane a flow path for said sample being hydrolyzed, said hydrolysis system membrane being substantially impermeable to said one or more hydrolytic agents while also being substantially permeable to urea and to urea hydrolysis products.

24. A method according to claim 23 further wherein one or more of said hydrolytic agents consist essentially of urease.

25. A method according to claim 19 wherein in step (a) and/or step (c) said first and/or second measure of total concentration of carbon dioxide, carbonic acid, bicarbonate and carbonate is obtained at an acidic pH.

26. A method according to claim 19 further comprising a step of estimating total organic carbon and/or total carbon.

27. A method according to claim 19 wherein the same measuring system is used for obtaining said first and second measures.

28. A method according to claim 19 wherein said sample of water before hydrolysis is hydrolyzed to become said hydrolyzed sample.

29. A method according to claim 19 wherein step (b) utilizes a hydrolysis system membrane substantially impermeable to one or more agents effective to hydrolyze entities which are hydrolyzed by urease while also being substantially permeable to water, carbon dioxide, carbonic acid, bicarbonate and carbonate.

30. A method according to claim 19 further comprising the steps of commingling a sample of said water with one or more agents effective to hydrolyze entities which are hydrolyzed by urease for such a time and at a pH and at a temperature effective substantially to hydrolyze entities which are hydrolyzed by urease to form said hydrolyzed sample commingled with said one or more agents, and thereafter separating said one or more agents from said hydrolyzed sample.

31. A method according to claim 19 further comprising the steps of commingling a sample of said water with one or more agents effective to hydrolyze entities which are hydrolyzed by urease for such a time and at a pH and at a temperature effective substantially to hydrolyze entities which are hydrolyzed by urease to form said hydrolyzed sample commingled with said one or more agents, and thereafter recovering carbon dioxide from said hydrolyzed sample commingled with said one or more agents.

32. A method according to claim 30 wherein said one or more agents are separated from said hydrolyzed sample utilizing a microporous membrane or an ultrafiltration membrane.

* * * * *